United States Patent
Ram Rakhyani et al.

(10) Patent No.: US 11,431,373 B2
(45) Date of Patent: Aug. 30, 2022

(54) VERTICALLY POLARIZED FIELD ENHANCER FOR WEARABLE DEVICES

(71) Applicant: Verily Life Sciences LLC, South San Francisco, CA (US)

(72) Inventors: Anil Kumar Ram Rakhyani, Union City, CA (US); Stephen O'Driscoll, San Francisco, CA (US)

(73) Assignee: VERILY LIFE SCIENCES LLC, South San Francisco, CA (US)

( * ) Notice: Subject to any disclaimer, the term of this patent is extended or adjusted under 35 U.S.C. 154(b) by 0 days.

(21) Appl. No.: 16/948,103

(22) Filed: Sep. 3, 2020

(65) Prior Publication Data
US 2021/0067188 A1   Mar. 4, 2021

Related U.S. Application Data

(60) Provisional application No. 62/895,643, filed on Sep. 4, 2019.

(51) Int. Cl.
*H04B 1/3827* (2015.01)
*H01Q 1/24* (2006.01)
(Continued)

(52) U.S. Cl.
CPC ............... *H04B 1/385* (2013.01); *H01Q 1/24* (2013.01); *H01Q 1/38* (2013.01); *H01Q 1/48* (2013.01);
(Continued)

(58) Field of Classification Search
CPC . H04B 1/385; H01Q 1/24; H01Q 1/48; H01Q 9/00; H01Q 1/38; H01Q 2213/003;
(Continued)

(56) References Cited

U.S. PATENT DOCUMENTS

| 8,203,497 B2 | 6/2012 | Sabban |
| 2011/0128198 A1 | 6/2011 | Sabban |
(Continued)

FOREIGN PATENT DOCUMENTS

| CN | 201797036 | 4/2011 |
| CN | 107611574 | 1/2018 |
(Continued)

OTHER PUBLICATIONS

International Application No. PCT/US2020/049402, International Search Report and Written Opinion, dated Nov. 27, 2020, 13 pages.

*Primary Examiner* — Eugene Yun
(74) *Attorney, Agent, or Firm* — Kilpatrick Townsend & Stockton LLP

(57) ABSTRACT

Disclosed herein is a wearable device having a horizontally polarized antenna and a vertically polarized antenna to gain the benefit of both types of polarization resulting in optimal signal transmission to and reception by a user's smartphone or mobile device. The wearable device includes a printed circuit board on a first plane along which plane the signal from the horizontally polarized signal will propagate. The printed circuit board includes a conductive ground plane and a trace antenna conductively coupled on one end of the trace to the conductive ground plane between which the horizontally polarized field is generated when the trace antenna is excited. A vertical field enhancer, parallel to the first plane and a distance from the trace antenna, is coupled to the ground plane, such that when the trace antenna is excited, a vertically polarized field is generated between the trace antenna and the vertical field enhancer.

16 Claims, 8 Drawing Sheets

(51) Int. Cl.
  *H01Q 1/48* (2006.01)
  *H04Q 9/00* (2006.01)
  *H01Q 1/38* (2006.01)

(52) U.S. Cl.
  CPC ......... *H04Q 9/00* (2013.01); *H04Q 2213/003* (2013.01)

(58) Field of Classification Search
  CPC .... H01Q 2209/43; H01Q 25/001; H01Q 9/42; H01Q 1/2225; H01Q 1/273; H01Q 21/24; A61B 5/0024; A61B 5/14532
  USPC ...................................................... 455/575.7
  See application file for complete search history.

(56) References Cited

U.S. PATENT DOCUMENTS

| | | | |
|---|---|---|---|
| 2016/0285157 A1 | 9/2016 | Aizawa | |
| 2017/0047647 A1* | 2/2017 | Jung | ........................ H01Q 1/48 |
| 2018/0294551 A1 | 10/2018 | Ryan et al. | |
| 2019/0157748 A1 | 5/2019 | Ozden | |

FOREIGN PATENT DOCUMENTS

| | | |
|---|---|---|
| GB | 2541769 | 3/2017 |
| WO | 2017026826 | 2/2017 |

\* cited by examiner

VERTICALLY POLARIZED FIELD ENHANCER FOR WEARABLE DEVICES

CROSS-REFERENCE TO RELATED APPLICATIONS

This application claims priority to U.S. Provisional Patent Application No. 62/895,643, filed Sep. 4, 2019, titled "Vertically Polarized Field Enhancer For Wearable Devices," the entirety of which is hereby incorporated by reference.

BACKGROUND

Wearable devices are small and often rely on communication with a nearby second device, like a smartphone, for processing the data from the sensors in the wearable device. For example, continuous glucose monitoring devices are small, patch-like devices that monitor the glucose level of the user and transmit the readings to the user's smartphone. An application on the user's smartphone is used to process the readings, alert the user to issues associated with the readings, and/or display the readings. The readings are transmitted using an antenna in the wearable device and are received with an antenna in the user's smartphone. These small wearable devices have limited space for an antenna. Accordingly, there are situations where the wearable device and the smartphone have poor or no connectivity. For example, the user's body acts as a shield that impedes transmission of the signal, particularly when the wearable device and the smartphone are on opposite sides of the body. The propagation features of the fields from antennae designed to fit within existing wearable devices are not well suited to travelling around the user's body. The result is that the wearable device and the smartphone may lose connection or have a poor connection, limiting the value of the continuous monitoring of the wearable device.

BRIEF SUMMARY

Disclosed herein is a wearable device having a horizontally polarized antenna and a vertically polarized antenna to gain the benefit of both types of polarization. The wearable device includes a printed circuit board on a first plane along which plane the signal from the horizontally polarized signal will propagate. The printed circuit board includes a conductive ground plane and a trace antenna conductively coupled on one end of the trace to the conductive ground plane. The trace antenna is configured to have an edge of the trace parallel to an edge of the conductive ground plane separated by a first distance. The wearable device also includes a vertical field enhancer on a second plane, parallel to the first plane, and separated from the first plane by a second distance. The wearable device also includes a conductive connector that couples the vertical field enhancer to the conductive ground plane. The wearable device also includes an integrated circuit that transmits a signal to excite the trace antenna. When the trace antenna is excited, a horizontally polarized field is induced between the trace antenna and the conductive ground plane, where the horizontally polarized field propagates in the first plane, and when the trace antenna is excited, a vertically polarized field is induced between the trace antenna and the vertical field enhancer, where the vertically polarized field propagates in a third plane orthogonal to the first plane.

Implementations may include one or more of the following features. In some embodiments, the space between the vertical field enhancer and the trace antenna includes a dielectric material. In some embodiments, the distance between the vertical field enhancer and the trace antenna is 2.5 millimeters. In some embodiments, the conductive connector is a battery clip. In some embodiments, the distance between the vertical field enhancer and the conductive connector is based on the desired frequency of the vertically polarized field. In some embodiments, the frequency of the vertically polarized field is 2.4 gigahertz. In some embodiments, the vertical field enhancer is stamped to a housing of the sensor. In some embodiments, the vertical field enhancer is nickel plated stainless steel. In some embodiments, the vertical field enhancer is a copper-nickel-zinc alloy.

BRIEF DESCRIPTION OF THE DRAWINGS

A further understanding of the nature and advantages of various examples may be realized by reference to the following figures.

Unless otherwise indicated, elements using the same indicator number are the same elements between differing figures. Some elements may include multiple of the same elements, which are indicated by a letter following the indicator number.

DETAILED DESCRIPTION

Figure 1:
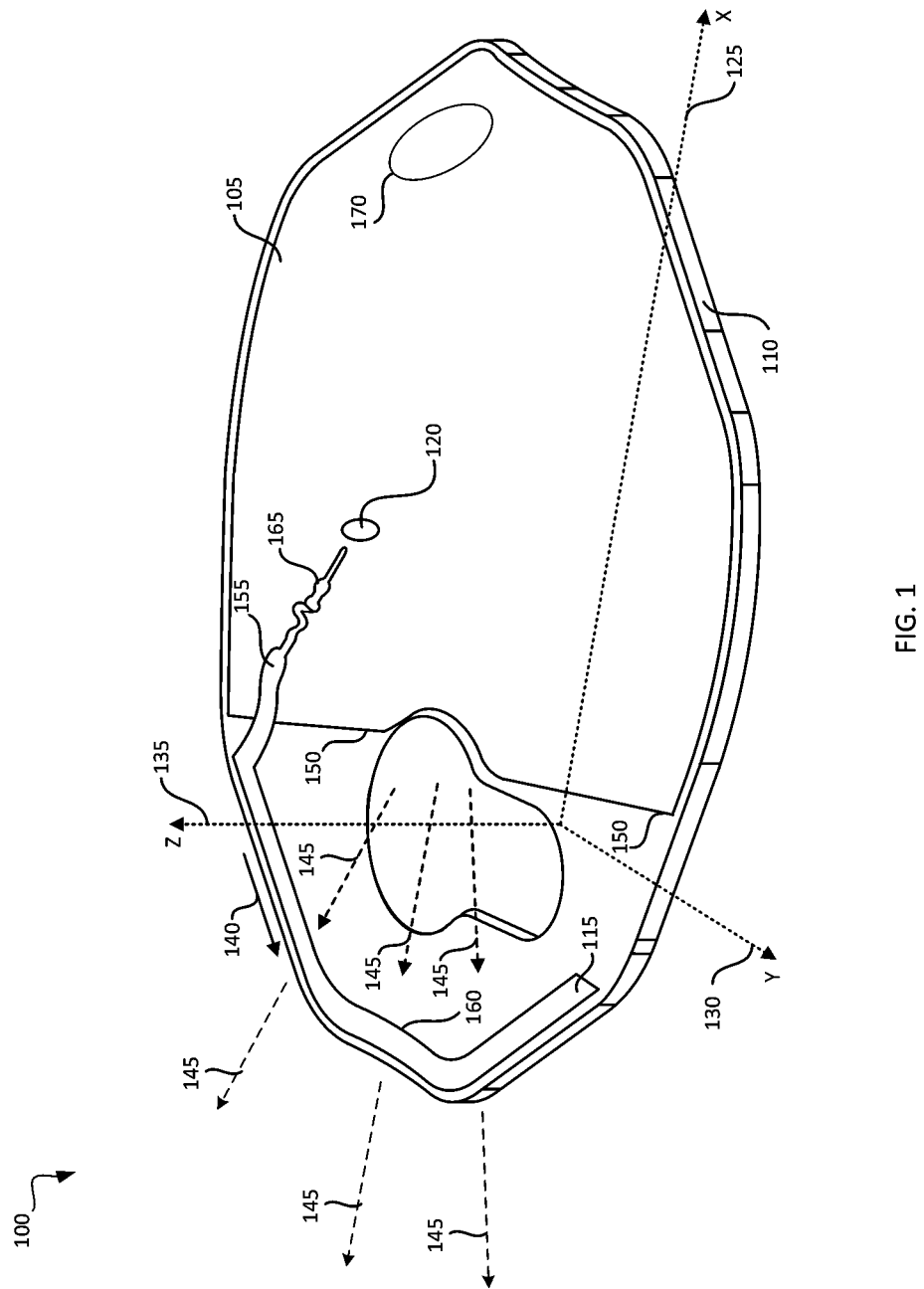
FIG. 1 illustrates an example wearable device with a horizontally polarized antenna, according to some embodiments.

Described herein are techniques for including both a horizontally polarized antenna and a vertically polarized antenna in a small, wearable device. Some small, wearable devices, such as continuous glucose monitors, heartrate monitors, respiration rate monitors, blood pressure monitors, blood oxygen saturation monitors, temperature monitors, sleep monitors, respiration or breathing monitors, wearable environmental exposure monitors (e.g., UV monitors, air quality monitors, or the like), or the like have an intentionally small footprint, are attached to the user's body, and benefit from continuous communication with the user's mobile device (e.g., a smartphone, tablet, or any other mobile electronic device having a transceiver). The wearable device communicates the monitored readings to the user's mobile device for processing, to alert the user of any issues with the user's glucose levels, and/or for further transmission to, for example, a parent or a doctor for monitoring purposes. In past systems of this type of small, wearable device, a horizontally polarized antenna may be used. While a horizontally polarized antenna works well for situations in which the user's mobile device is placed away from the user's body on the same side of the user on which the wearable device is located, it is not well suited to transmitting around the user's body or even to other locations on the user's body due to the propagation of the horizontally polarized field and the insulating features of the user's body. Therefore, when the mobile device is on the opposite side of the user's body as the wearable device or when the mobile device is on the user's body (e.g., in a purse held closely, in a pocket, or on a belt clip), the signal from the wearable device at the mobile device is weak or non-existent.

As discussed within this disclosure, a horizontally polarized antenna is an antenna that transmits a field that propagates along the plane of the printed circuit board of the wearable device. A vertically polarized antenna, as used for the purposes of this disclosure, is an antenna that transmits a field that propagates along a plane orthogonal to the printed circuit board of the wearable device. Wearable devices are placed on the user's body, typically, such that the printed circuit board is flat against the user's body. The human body acts as a lossy dielectric, and in such wearable devices, the field from the antenna is launched at the interface of the human body and air (i.e., the air-dielectric interface). Horizontally polarized fields are launched parallel to the air-dielectric interface, and vertically polarized fields are launched normal to (i.e., perpendicular to) the air-dielectric interface.

A solution to the problem of weak or no signal between the wearable device and the mobile device based on location of the devices with respect to the user's body is to incorporate a vertically polarized antenna into the wearable device in addition to the horizontally polarized antenna. The vertically polarized fields are able to travel around the human body much more effectively than the horizontally polarized fields. In past systems, vertically polarized antenna take substantial space within the device and increase the thickness of the wearable device to accommodate the antenna. Accordingly, existing small, wearable devices do not include both horizontally and vertically polarized antennae. In the solution described herein, the vertically polarized antenna fits within the existing wearable device. As such, the thickness of the wearable device is not increased. The thickness of the vertically polarized antenna is, in some embodiments, less than three (3) millimeters thick. One example solution includes utilizing the antenna trace as both the antenna trace of the horizontally polarized antenna and the antenna trace of the vertically polarized antenna. A vertical field enhancer is used with the antenna trace to generate the vertically polarized field. The vertical field enhancer minimizes the size and space needed for the vertically polarized antenna.

As mentioned above, the human body acts as a lossy dielectric. This disclosure discusses wearable devices, however, this problem and solution is applicable to any device attached to an object that is a lossy dielectric (e.g., a wireless sensor on a drum of milk, wine, or the like) for, for example, tracking the location of the object.

FIG. 1 illustrates an example wearable device 100 having a conductive ground plane 105 on a printed circuit board 110. The wearable device 100 also includes a trace antenna 115, sensor component 170, and a transceiver integrated circuit ("IC") 120 on the printed circuit board 110. Shown in FIG. 1 is the X 125, Y 130, Z 135 axes on which the printed circuit board 110 is oriented. For the purposes of this description, the printed circuit board 110, conductive ground plane 105, and trace antenna 115 are all on a first plane, which in the described axes is the X 125, Y 130 plane at a Z 135 value of zero.

The conductive ground plane 105 can be any conductive material including, for example, copper. The conductive ground plane has an edge 150. The conductive ground plane may be, for example, a thin copper layer (e.g., copper foil) upon the printed circuit board 110. The printed circuit board 110 is a self-contained module of interconnected electronic components including the trace antenna 115 and the transceiver integrated circuit 120. The printed circuit board 110 can include a substrate made of, for example, fiberglass epoxy resin or a paper reinforced phenolic resin, for example. The ground plane 105 can be a layer on at least portions of the printed circuit board 110 separated by an insulating material from other layers.

The trace antenna 115 may be a copper trace on the printed circuit board 110. As shown in FIG. 1, the wearable device 100 has an overall octagonal shape, and the trace antenna 115 is at an edge portion of the wearable device 100. In some embodiments, the wearable device 100 and/or the printed circuit board 110 may be any other suitable shape including circle, oval, square, triangle, rectangle, star, heart, and so forth. The inside edge 160 of the trace antenna 115 is at a distance from the edge 150 of the ground plane 105. The distance between edge 150 and trace antenna 115 may be any suitable distance such that the electromagnetic field can be generated between them. For example, as measured perpendicularly from the midpoint of trace antenna 115, the trace antenna 115 may be a distance of approximately one tenth (1/10) of the desired wavelength of the electromagnetic field from the edge 150. The antenna trace 115 is electrically coupled to the ground plane 105 at point 155. At point 165, antenna trace 115 is electrically coupled to the transceiver integrated circuit 120 using a connector trace.

The transceiver integrated circuit 120 is configured to perform functions relevant to the wearable device including to send a signal to the trace antenna 115 to excite the trace antenna 115, such as to wirelessly transmit sensor data from the sensor device to a remote wireless device such as a user's smartphone. The transceiver integrated circuit 120 may be configured to perform other functions as well.

The sensor component 170 may be any sensor or portion of a sensor for measuring physiological parameters (e.g., glucose levels, heart rate, or the like) of the user. The sensor component 170 may sense physiological signals from the user and generate a signal representing the sensed physiological signal of the desired physiological parameter. In some embodiments, the physiological sensor component 170 may be separate from the printed circuit board 110 and electrically coupled to the circuitry on the printed circuit board 110 for providing a signal representing the sensed physiological parameters to the transceiver integrated circuit 120. Sensor component 170 may be electrically coupled to transceiver integrated circuit 120 such that transceiver integrated circuit 120 can transmit a signal representing the information from sensor component 170 via the generated electromagnetic fields 145.

In use, the transceiver integrated circuit 120 transmits a signal to antenna trace 115. The signal travels as shown by arrow 140 and excites the antenna trace 115. Excitation of the antenna trace 115 generates an electromagnetic field 145 that propagates horizontally (i.e., parallel to the plane of the printed circuit board) between the edge 160 of the antenna trace 115 and the edge 150 of the ground plane 105. This generated field 145 transmits signals for the user's mobile device to receive.

Figure 2:
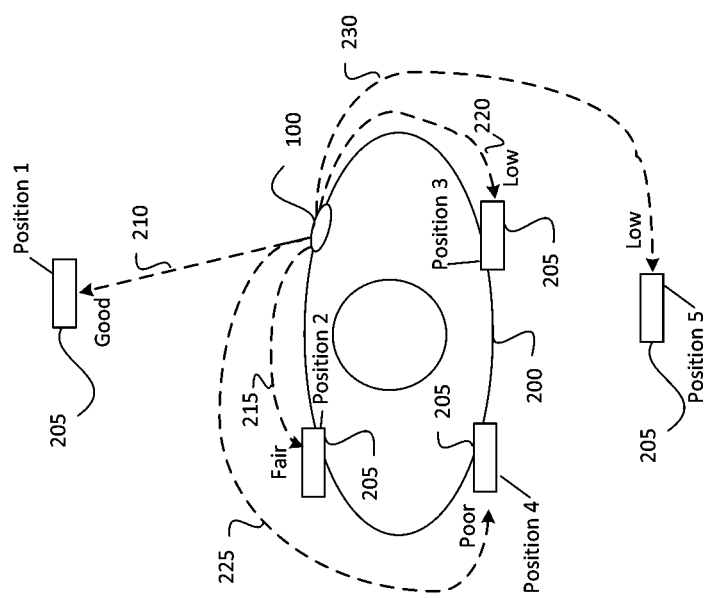
FIG. 2 illustrates example device locations using the wearable device of FIG. 1, according to some embodiments.

FIG. 2 illustrates a top-down view of a person's body indicating different locations of the mobile device 205 of the user in relation to the location of the wearable device 100. The user can be any person having a wearable device 100 and a mobile device 205. The user's body 200 at least partially shields the radiation pattern emitting from the antenna 115 in the wearable device 100 such that the signal must travel around the user's body 200 when the user has the mobile device 205 on a different side of the user's body 200 than the wearable device 100.

Wearable device 100 may be located anywhere on the user's body 200 such that sensors in the wearable device 100 may monitor one or more physiological parameters (e.g., glucose levels, heart rate, or the like) of the user. In the example of a continuous glucose monitor, the wearable device 100 may be located on the user's abdomen. In FIG. 2, the wearable device 100 is depicted on the right abdomen of the user's body 200.

Mobile device 205 may be any suitable mobile device that can receive signals from the wearable device 100. Mobile device 205 may be, for example, a smartphone, a tablet, a laptop computer, or any other mobile computing device. For the purposes of FIG. 2, mobile device 205 is shown at different positions, which are labelled as position 1, position 2, position 3, position 4, and position 5.

When mobile device 205 is in position 1, it is off the user's body 200 and on the same side of the user's body 200 as the wearable device 100. For example, the user may have left the mobile device on a table in front of himself or perhaps is holding the mobile device 205 in his hand. In this position, the horizontally polarized antenna transmits a signal 210 to the mobile device 205 that has a good signal reception at the mobile device 205.

When the mobile device 205 is in position 2, it is on the user's body on the same side of the user's body 200 as the wearable device 100. For example, the user may have the phone clipped to his or her belt. In this position, the user's body shields some of the electromagnetic field, and the horizontally polarized antenna transmits a signal 215 to the mobile device 205 that has a fair signal reception at the mobile device 205.

When the mobile device 205 is in position 3, it is on the user's body on the opposite side of the user's body 200 as the wearable device 100 from front to back, however it is on the same left or right side of the user's body 200 (e.g., the wearable device 100 is on his right abdomen and the mobile device 205 is in his back right pocket). In this position, the user's body shields much of the electromagnetic field, and the horizontally polarized antenna transmits a signal 220 to the mobile device 205 that has a low signal reception at the mobile device 205.

When the mobile device 205 is in position 4, it is on the user's body on the opposite side across of the user's body 200 as the wearable device 100 from front to back and left to right. For example, the user may have the phone in his back pocket on the opposite side of his body 200 (e.g., the wearable device 100 is on his right abdomen and the mobile device 205 is in his back left pocket). In this position, the user's body shields most of the electromagnetic field, and the horizontally polarized antenna transmits a signal 225 to the mobile device 205 that has a such a poor signal reception that it loses connection at the mobile device 205.

When the mobile device 205 is in position 5, it is off the user's body on the opposite side of the user's body 200 as the wearable device 100. For example, mobile device 205 may be behind the user (e.g., the wearable device 100 is on his right abdomen and the mobile device 205 is behind him on a table). In this position, the user's body shields much of the electromagnetic field, and the horizontally polarized antenna transmits a signal 230 to the mobile device 205 that has a low signal reception at the mobile device 205.

As seen by FIG. 2, the horizontally polarized antenna provides useful signal transmission for some circumstances (e.g., the mobile device is off the body and on the same side of the body as the wearable device), but in some circumstances (e.g., the mobile device is across the body and on the opposite side as the wearable device), the signal can be significantly attenuated by the time it reaches the mobile device 205.

Figure 3:
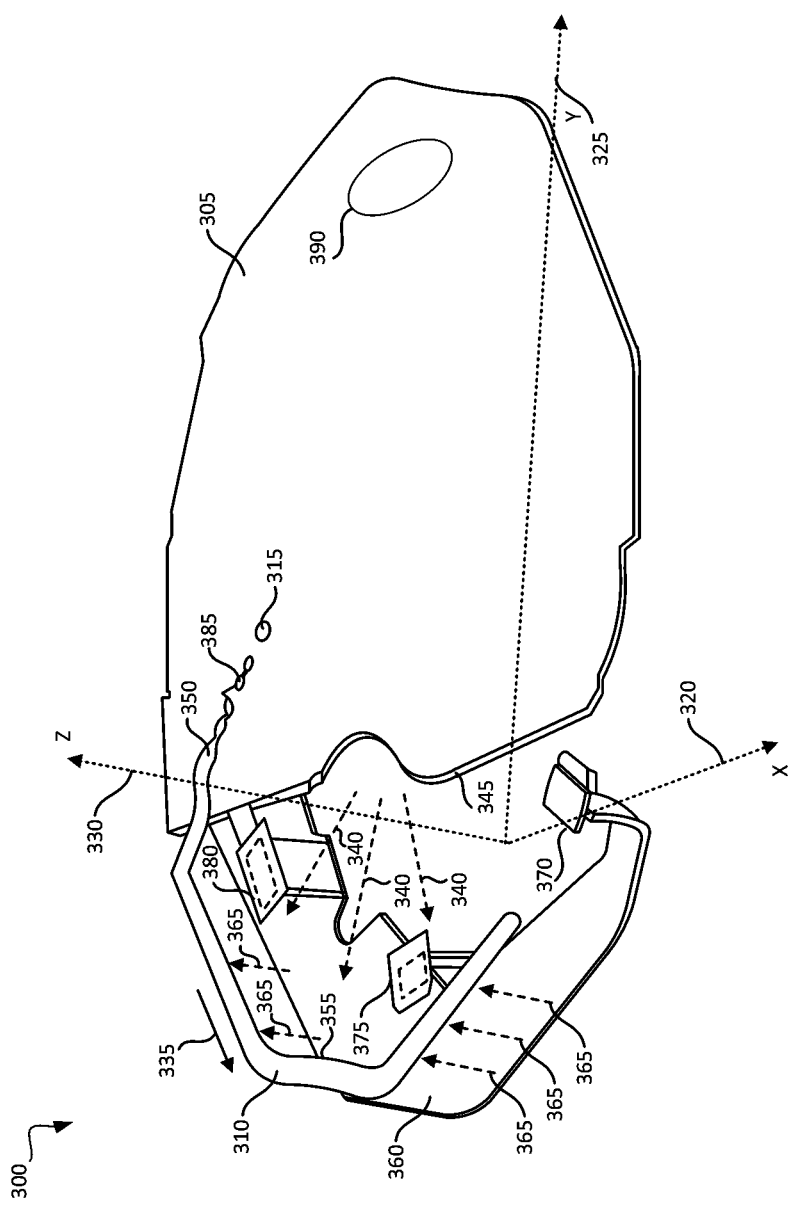
FIG. 3 illustrates an example wearable device with a horizontally polarized antenna and a vertically polarized antenna using a vertical field enhancer, according to some embodiments.

FIG. 3 illustrates a wearable device 300 having a horizontally polarized antenna and a vertically polarized antenna. The wearable device 300 has a conductive ground plane 305 can be similar to conductive ground plane 105. Conductive ground plane 305 may be a copper layer on a printed circuit board. The printed circuit board, not shown, in the configuration shown in FIG. 3 is above the conductive ground plane 305. The wearable device 300 includes a trace antenna 310, a transceiver integrated circuit 315, a sensor component 390, and a vertical field enhancer 360. Shown in FIG. 3 is the X 320, Y 325, Z 330 axes on which the printed circuit board is oriented. For the purposes of this description, the printed circuit board, conductive ground plane 305, and trace antenna 310 are all on a first plane, which in the described axes is the X 320, Y 325 plane at a Z 330 value of zero. The wearable device may be, for example, a continuous glucose monitor, heartrate monitor, respiration rate monitor, blood pressure monitor, blood oxygen saturation monitor, or the like.

The conductive ground plane 305 can be any conductive material including, for example, copper. The conductive ground plane has an edge 345. The conductive ground plane may be, for example, a thin copper layer (e.g., copper foil) on the printed circuit board. The ground plane 305 can be a layer on at least portions of the printed circuit board separated by an insulating material from other layers.

The trace antenna 310 may be a copper trace on the printed circuit board. As shown in FIG. 3, the wearable device 300 has an overall octagonal shape, and the trace antenna 310 is at an edge portion of the wearable device 300. In some embodiments, the wearable device 300 and/or the printed circuit board may be any other suitable shape including circle, oval, square, triangle, rectangle, star, heart, and so forth. The inside edge 355 of the trace antenna 310 is a distance from the edge 345 of the ground plane 305. The antenna trace 310 is electrically coupled to the ground plane 305 at point 350. At point 385, antenna trace 310 is electrically coupled to the transceiver integrated circuit 315 using a connector trace.

The transceiver integrated circuit 315 is configured to perform functions relevant to the wearable device 300 including to send a signal to the trace antenna 310 to excite the trace antenna 310. The transceiver integrated circuit 315 may be configured to perform other functions as well.

The vertical field enhancer 360 can be a conductive material such as, for example, pure copper, nickel plated stainless steel, a copper-nickel-zinc alloy, or a phosphor bronze alloy. The vertical field enhancer 360 is in a second plane substantially parallel to the first plane of the conductive ground plane 305 and trace antenna 310. In some embodiments, the vertical field enhancer 360 is a thin copper layer stamped onto the inside housing (shown in FIGS. 6 and 7) of the wearable device 300. In some embodiments, the vertical field enhancer 360 is a conductive layer that has structural supports such as those shown at 370, 375, and 380.

The second plane is a distance away from the first plane. In other words, the vertical field enhancer 360 is a distance along the Z-axis from the antenna trace 310. The distance between the vertical field enhancer 360 and the antenna trace 310 is based on the desired wavelength of the field. The distance between the vertical field enhancer 360 and the antenna trace 310 may contain air in some embodiments. In some embodiments, the distance between the vertical field enhancer and the antenna trace 310 may contain a dielectric material. The vertical field enhancer is conductively coupled via a connector (not shown) to the conductive ground plane 305. The distance between the portion of the vertical field enhancer 360 over the antenna trace 310 and the connector may be determined based on the desired frequency of the vertically polarized field.

The sensor component 390 may be any sensor or portion of a sensor for measuring physiological parameters (e.g., glucose levels, heart rate, or the like) of the user. The sensor component 390 may sense physiological signals from the user and generate a signal representing the sensed physiological signal of the desired physiological parameter. In some embodiments, the physiological sensor component 390 may not be printed on the printed circuit board and may be electrically coupled to the circuitry on the printed circuit board for providing a signal representing the sensed physiological parameters to the transceiver integrated circuit 315. Sensor component 390 may be electrically coupled to transceiver integrated circuit 315 such that transceiver integrated circuit 315 can transmit a signal representing the information from sensor component 390 via the generated electromagnetic fields 365 and 340.

In use, the transceiver integrated circuit 315 transmits a signal to antenna trace 310. The signal travels as shown by arrow 335 and excites the antenna trace 310. Excitation of the antenna trace 310 generates an electromagnetic field 340 that propagates horizontally (i.e., in the first plane containing the conductive ground plane 305 and the antenna trace 310) between the edge 355 of the antenna trace 310 and the edge 345 of the ground plane 305 and radiates outward from the antenna trace 310 in the horizontal plane. This generated field 340 is horizontally polarized to transmit signals for the user's mobile device to receive. In addition, excitation of the antenna trace 310 generates an electromagnetic field 365 that propagates vertically (e.g., perpendicular to the first plane containing the conductive ground plane 305 and the antenna trace 310) between the vertical field enhancer 360 and the antenna trace 310 and radiates outward from the antenna trace 310 in the vertical plane. This generated field 365 is vertically polarized (i.e., radiating orthogonally to the plane of the printed circuit board) by the interaction between the antenna trace 310 and the vertical field enhancer 360 to transmit signals for the user's mobile device to receive.

Inclusion of both the vertically polarized antenna (the vertical field enhancer 360 and antenna trace 310) and the horizontally polarized antenna (the conductive ground plane 305 and antenna trace 310) in wearable device 300 provides the benefits of both polarizations. While horizontally polarized fields provide good signal propagation for same side of the body communication between the wearable device and the mobile device, the vertically polarized fields provide better signal propagation for opposite side of the body communication. Because the vertically polarized field propagates out from the user's body, the vertically polarized field is better suited to travel around the user's body. When both are combined in a single device, the benefits of both types of antennae are gained without reducing the value (e.g., the signal strength) of either antenna.

Figure 4:
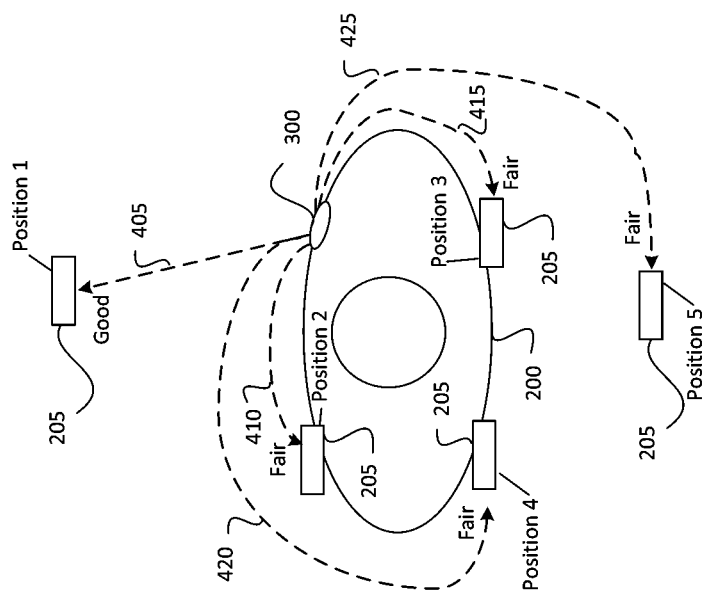
FIG. 4 illustrates example device locations using the wearable device of FIG. 3, according to some embodiments.

FIG. 4 illustrates different locations of the mobile device 205 of the user in relation to the location of the wearable device 300. This is similar to the illustration of FIG. 2, however now the wearable device 300 includes both a horizontally polarized antenna and a vertically polarized antenna as described with respect to FIG. 3. FIG. 4 is a top-view of the user's body 200. The user can be any person having a wearable device 300 and a mobile device 205. The user's body 200 shields some of the radiation pattern emitting from the antenna in the wearable device 300 such that the signal must travel around the user's body 200 when the user has the mobile device 205 on a different side of the user's body 200 than the wearable device 300.

Wearable device 300 may be located anywhere on the user's body 200 such that sensors in the wearable device 300 may monitor the user's vitals as needed. In the example of a continuous glucose monitor, the wearable device 300 may be located on the user's abdomen. In FIG. 2, the wearable device 300 is depicted on the right abdomen of the user's body 200.

For the purposes of FIG. 4, mobile device 205 is moving positions, which are labelled as position 1, position 2, position 3, position 4, and position 5. These positions are the same as those described with respect to FIG. 2.

When mobile device 205 is in position 1, it is off the user's body 200 and on the same side of the user's body 200 as the wearable device 300. For example, the user may have left the mobile device on a table in front of himself or perhaps is holding the mobile device 205 in his hand. In this position, the antennae within wearable device 300 transmit a signal 405 to the mobile device 205 that has a good signal reception at the mobile device 205. The good signal reception at position 1 is largely due to the horizontally polarized antenna.

When the mobile device 205 is in position 2, it is on the user's body on the same side of the user's body 200 as the wearable device 300. For example, the user may have the phone clipped to his or her belt or in his or her pocket. In this position, the user's body 200 shields some of the field, and the antennae within wearable device 300 transmit a signal 410 to the mobile device 205 that has a fair signal reception at the mobile device 205. The fair signal reception at position 2 is largely due to the horizontally polarized antenna.

When the mobile device 205 is in position 3, it is on the user's body on the opposite side of the user's body 200 as the wearable device 300 from front to back, however it is on the same left or right side of the user's body 200 (e.g., the wearable device 300 is on his right abdomen and the mobile device 205 is in his back right pocket). In this position, the user's body 200 shields some of the field, and the antennae within wearable device 300 transmit a signal 415 to the mobile device 205 that has a fair signal reception at the mobile device 205. As noted with respect to FIG. 1, at position 3, the horizontally polarized antenna had a low signal reception. The fair signal reception at position 3 is largely due to the vertically polarized antenna transmitting the signal 415 around the user's body 200.

When the mobile device 205 is in position 4, it is on the user's body on the opposite side across of the user's body 200 as the wearable device 300 from front to back and left to right. For example, the user may have the phone in his back pocket on the opposite side of his body 200 (e.g., the wearable device 300 is on his right abdomen and the mobile device 205 is in his back left pocket). In this position, the user's body 200 shields some of the field, and the antennae within wearable device 300 transmit a signal 420 to the mobile device 205 that has a fair signal reception at the mobile device 205. As noted with respect to FIG. 1, at position 4, the horizontally polarized antenna had such a low signal reception, there was no connection. The fair signal reception at position 4 is largely due to the vertically polarized antenna transmitting the signal 420 around the user's body 200.

When the mobile device 205 is in position 5, it is off the user's body on the opposite side of the user's body 200 as the wearable device 100. For example, mobile device 205 may be behind the user (e.g., the wearable device 100 is on his right abdomen and the mobile device 205 is behind him on a table). In position 5, the user's body 200 shields some of the field, and the antennae within wearable device 300 transmit a signal 425 to the mobile device 205 that has a fair signal reception at the mobile device 205. As noted with respect to FIG. 1, at position 5, the horizontally polarized antenna had a low signal reception. The fair signal reception at position 5 is largely due to the vertically polarized antenna transmitting the signal 425 around the user's body 200.

As shown in FIG. 4, the horizontally polarized antenna in combination with the vertically polarized antenna within wearable device 300 provides useful signal transmission for all close-body circumstances such that within a certain distance (e.g., ten feet), regardless of location with respect to the user's body, the wearable device 300 maintains connection with the mobile device 205.

Figure 5:
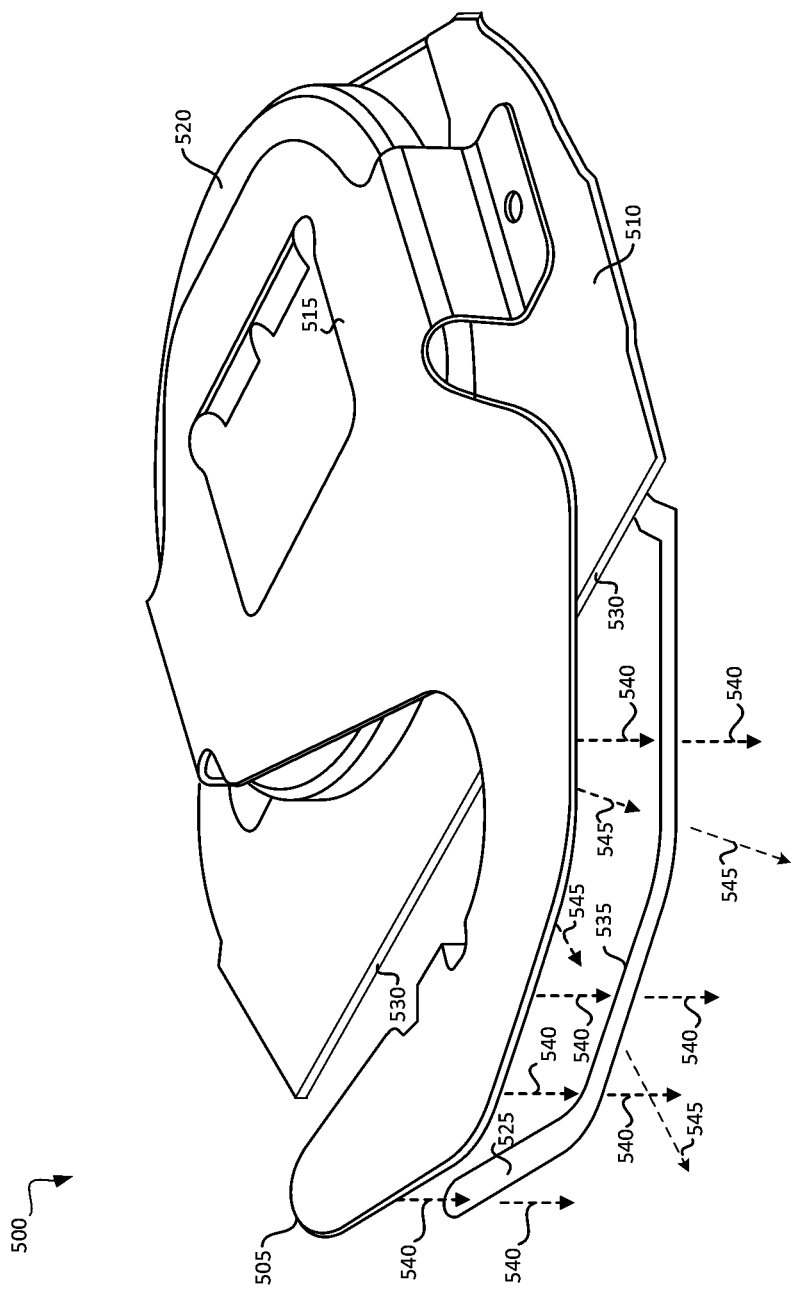
FIG. 5 illustrates an example wearable device with a vertical field enhancer and utilizing the battery clip as a connector, according to some embodiments.

FIG. 5 illustrates a wearable device 500 having a vertical field enhancer 505 that is connected to the ground plane 510 through the battery clip 515. In other words, the batter clip 515 is the conductive connector that couples the vertical field enhancer 505 to the conductive ground plane 510. Battery clip 515 conductively couples the vertical field enhancer 505 to the conductive ground plane 510. The battery clip 515 holds battery 520 in wearable device 500. The ground plane 510 is substantially the same as ground planes 105 and 305. Vertical field enhancer 505 is substantially the same as vertical field enhancer 360. Antenna trace 525 is substantially the same as antenna traces 115 and 310. Accordingly, when the transceiver integrated circuit (not shown) transmits a signal to excite antenna trace 525, vertically polarized field 540 is generated between vertical field enhancer 505 and antenna trace 525. Further horizontally polarized field 545 is generated between the edge 530 of conductive ground plane 510 and the edge 535 of antenna trace 525.

Figure 6:
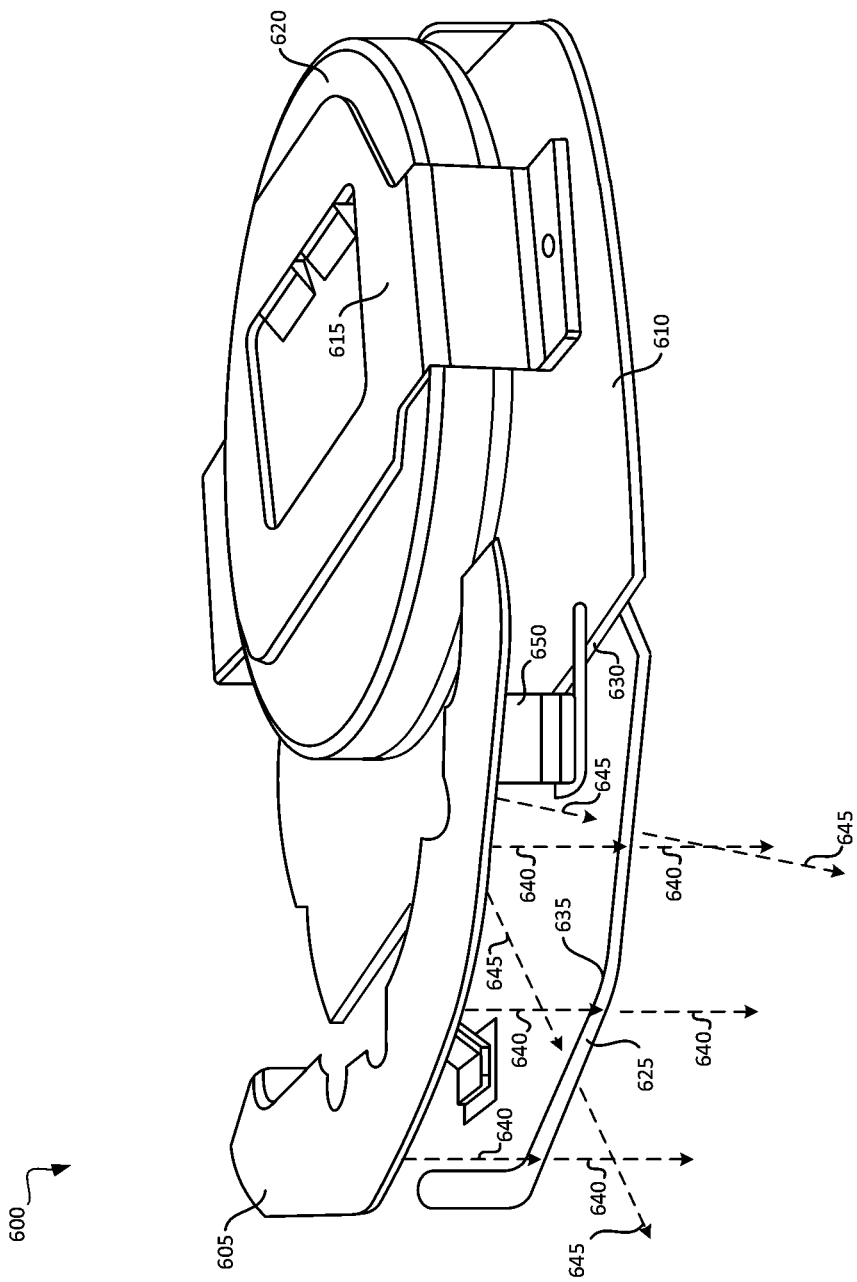
FIG. 6 illustrates an example wearable device with a vertical field enhancer with a supporting connector, according to some embodiments.

FIG. 6 illustrates wearable device 600 having a vertical field enhancer 605 that is connected to the ground plane 610 through connection point 650. Connection point 650 conductively couples the vertical field enhancer 605 to the conductive ground plane 610. Connection point 650 may be, for example, a conductive spring or other support structure. In other words, connection point 650 is a conductive connector that is a standalone conductive material that couples vertical field enhancer 605 to conductive ground plane 610. The battery clip 615 holds battery 620 in wearable device 600. In this embodiment, battery clip 615 does not conductively couple to vertical field enhancer 605. The ground plane 610 is substantially the same as ground planes 105, 305, and 510. Vertical field enhancer 605 is substantially the same as vertical field enhancers 360 and 505. Antenna trace 625 is substantially the same as antenna traces 115, 310, and 525. Accordingly, when the transceiver integrated circuit (not shown) transmits a signal to excite antenna trace 625, vertically polarized field 640 is generated between vertical field enhancer 605 and antenna trace 625. Further horizontally polarized field 645 is generated between the edge 630 of conductive ground plane 610 and the edge 635 of antenna trace 625.

Figure 7:
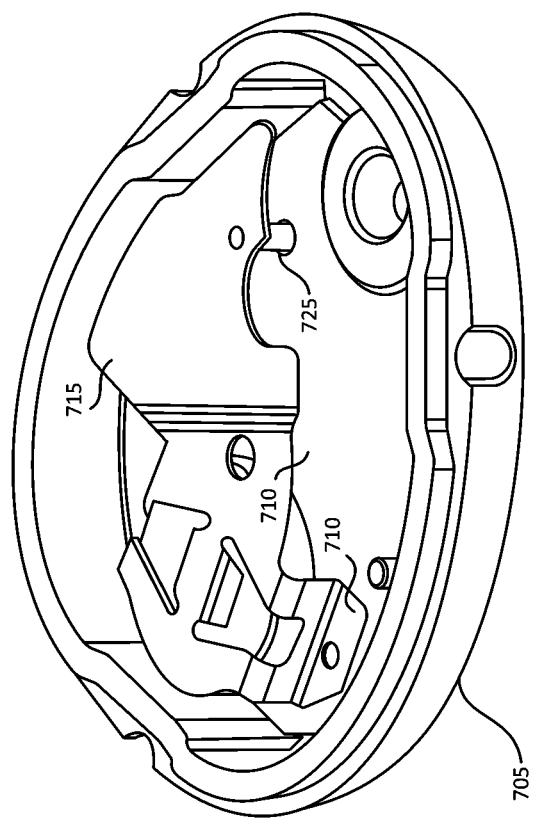
FIG. 7 illustrates another example wearable device with a vertical field enhancer, according to some embodiments.

FIG. 7 illustrates an example wearable device 700. Wearable device 700 depicts the upper housing 705 detached from the lower housing (not shown) to provide an interior view of some components of the wearable device 700. The battery clip 710 provides the conductive connection between the vertical field enhancer 715 and the ground plane 720. Support 725 provides non-conductive support to the vertical field enhancer 715 to ensure the appropriate distance is maintained from the antenna trace (not shown).

Figure 8:
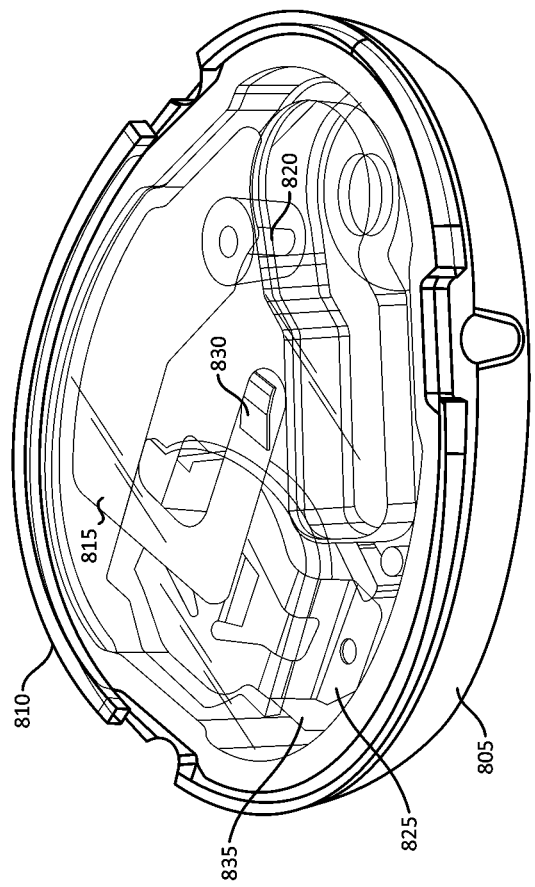
FIG. 8 illustrates another example wearable device with a vertical field enhancer, according to some embodiments.

FIG. 8 illustrates an example wearable device 800. Wearable device 800 depicts the upper housing 805 and a clear lower housing 810 to provide an interior view of some components of the wearable device 800. The vertical field enhancer 815 is stamped on the lower housing 810. The vertical field enhancer 815 may be, for example, a copper stamp. A non-conductive support 820 for the vertical field enhancer 815 can ensure the vertical field enhancer 815 remains in place. Connection point 830 conductively couples the vertical field enhancer 815 to the ground plane 835. The battery clip 825 is not coupled to the vertical field enhancer 815 in this embodiment.

Different arrangements of the components depicted in the drawings or described above, as well as components and steps not shown or described are possible. Similarly, some features and sub-combinations are useful and may be employed without reference to other features and sub-combinations. Embodiments of the present disclosure have been described for illustrative and not restrictive purposes, and alternative embodiments will become apparent to readers of this patent. In certain cases, method steps or operations may be performed or executed in differing order, or operations may be added, deleted or modified. It can be appreciated that, in certain aspects of the present disclosure, a single component may be replaced by multiple components, and multiple components may be replaced by a single component, to provide an element or structure or to perform a given function or functions. Except where such substitution would not be operative to practice certain embodiments of the present disclosure, such substitution is considered within the scope of the present disclosure.

It is to be understood that the figures and descriptions of embodiments of the present disclosure have been simplified to illustrate elements that are relevant for a clear understanding of the present disclosure. Those of ordinary skill in the art will recognize, however, that these and other elements may be desirable. However, because such elements are well known in the art, and because they do not facilitate a better understanding of the present disclosure, a discussion of such elements is not provided herein. It should be appreciated that the figures are presented for illustrative purposes and not as construction drawings. Omitted details and modifications or alternative embodiments are within the purview of persons of ordinary skill in the art.

It can be appreciated that, in certain aspects of the present disclosure, a single component may be replaced by multiple components, and multiple components may be replaced by a single component, to provide an element or structure or to perform a given function or functions. Except where such substitution would not be operative to practice certain embodiments of the present disclosure, such substitution is considered within the scope of the present disclosure. A recitation of "a", "an" or "the" is intended to mean "one or more" unless specifically indicated to the contrary.

Use herein of the word "or" is intended to cover inclusive and exclusive OR conditions. In other words, A or B or C includes any or all of the following alternative combinations as appropriate for a particular usage: A alone; B alone; C alone; A and B only; A and C only; B and C only; and A and B and C.

The examples presented herein are intended to illustrate potential and specific implementations of the present disclosure. It can be appreciated that the examples are intended primarily for purposes of illustration of the present disclosure for those skilled in the art. There may be variations to these diagrams or the operations described herein without departing from the spirit of the present disclosure. For instance, in certain cases, method steps or operations may be performed or executed in differing order, or operations may be added, deleted or modified.

Furthermore, whereas particular embodiments of the present disclosure have been described herein for the purpose of illustrating the present disclosure and not for the purpose of limiting the same, it will be appreciated by those of ordinary skill in the art that numerous variations of the details, materials and arrangement of elements, steps, structures, and/or parts may be made within the principle and scope of the present disclosure without departing from the present disclosure as described in the claims.

What is claimed is:

1. A sensor for wearing on a body of a user, the sensor comprising:
    a printed circuit board on a first plane, the printed circuit board comprising:
        a conductive ground plane, and
        a trace antenna conductively coupled on one end of the trace antenna to the conductive ground plane and configured to have an edge of the trace antenna separated by a first distance from an edge of the conductive ground plane;
    a vertical field enhancer on a second plane parallel to the first plane and separated from the first plane by a second distance;
    a conductive connector that couples the vertical field enhancer to the conductive ground plane; and
    a transceiver integrated circuit electrically coupled to the trace antenna to transmit signals to excite the trace antenna, wherein the trace antenna and the conductive ground plane are configured to generate a horizontally polarized electromagnetic field that propagates in the first plane, and wherein the trace antenna and the vertical field enhancer are configured to generate a vertically polarized electromagnetic field that propagates in a third plane orthogonal to the first plane, and wherein, when the trace antenna is excited, the vertically polarized electromagnetic field is generated between the trace antenna and the vertical field enhancer.

2. The sensor of claim 1, wherein a space between the vertical field enhancer and the trace antenna consists of air.

3. The sensor of claim 1, wherein a space between the vertical field enhancer and the trace antenna comprises a dielectric material.

4. The sensor of claim 1, wherein the conductive connector is a standalone conductive material soldered between the conductive ground plane and the vertical field enhancer.

5. The sensor of claim 1, wherein the conductive connector is a battery clip.

6. The sensor of claim 1, wherein a distance between the vertical field enhancer and the conductive connector is based on a desired frequency of the vertically polarized electromagnetic field.

7. The sensor of claim 1, wherein the vertical field enhancer comprises at least one of nickel-plated stainless steel, a copper-nickel-zinc alloy, pure copper, or a phosphor bronze alloy.

8. The sensor of claim 1, wherein the vertical field enhancer is stamped to a housing of the sensor.

9. A sensor device for wearing on a body of a user, the sensor device comprising:
    a printed circuit board on a first plane, the printed circuit board comprising:
        a conductive ground plane,
        a trace antenna conductively coupled on one end to the conductive ground plane and configured to have an edge of the trace antenna separated by a first distance from an edge of the conductive ground plane, and
        a transceiver integrated circuit electrically coupled to the trace antenna to transmit signals to excite the trace antenna;
    a vertical field enhancer on a second plane parallel to the first plane and separated from the first plane by a second distance, wherein a conductive connector couples the vertical field enhancer to the conductive ground plane, wherein the trace antenna and the conductive ground plane are configured to generate a horizontally polarized electromagnetic field that propagates in the first plane, and wherein the trace antenna and the vertical field enhancer are configured to generate a vertically polarized electromagnetic field that propagates in a third plane orthogonal to the first plane, and wherein, when the trace antenna is excited, the vertically polarized electromagnetic field is generated between the trace antenna and the vertical field enhancer;
    a physiological sensor for sensing physiological signals from the user, wherein the physiological sensor is electrically coupled to the transceiver integrated circuit; and
    a housing within which the printed circuit board, the vertical field enhancer, and the physiological sensor are enclosed.

10. The sensor device of claim 9, wherein a space between the vertical field enhancer and the trace antenna consists of air.

11. The sensor device of claim 9, wherein a space between the vertical field enhancer and the trace antenna comprises a dielectric material.

12. The sensor device of claim 9, wherein the conductive connector is a standalone conductive material soldered between the conductive ground plane and the vertical field enhancer.

13. The sensor device of claim 9, wherein the conductive connector is a battery clip.

14. The sensor device of claim 9, wherein a distance between the vertical field enhancer and the conductive connector is based on a desired frequency of the vertically polarized electromagnetic field.

15. The sensor device of claim 9, wherein the vertical field enhancer comprises at least one of nickel-plated stainless steel, a copper-nickel-zinc alloy, pure copper, or a phosphor bronze alloy.

16. The sensor device of claim 9, wherein the vertical field enhancer is stamped to the housing.

\* \* \* \* \*